United States Patent
Suri et al.

(10) Patent No.: US 6,614,453 B1
(45) Date of Patent: Sep. 2, 2003

(54) METHOD AND APPARATUS FOR MEDICAL IMAGE DISPLAY FOR SURGICAL TOOL PLANNING AND NAVIGATION IN CLINICAL ENVIRONMENTS

(75) Inventors: Jasjit S. Suri, Mayfield Heights, OH (US); Ruhul Quddus, Philadelphia, PA (US); Yansun Xu, Solon, OH (US)

(73) Assignee: Koninklijke Philips Electronics, N.V., Eindhoven (NL)

( * ) Notice: Subject to any disclaimer, the term of this patent is extended or adjusted under 35 U.S.C. 154(b) by 0 days.

(21) Appl. No.: 09/565,253

(22) Filed: May 5, 2000

(51) Int. Cl.[7] .............................. G06F 3/00; G06F 9/46; A61B 5/05
(52) U.S. Cl. ................ 345/764; 345/419; 345/848; 345/961; 600/425; 600/427; 600/407; 709/315; 709/332
(58) Field of Search ................. 345/764, 424, 345/419, 427, 619, 643, 771, 773, 848, 849, 852, 961; 600/407, 410–411, 416, 425, 427; 709/315–316, 313, 330–332

(56) References Cited

U.S. PATENT DOCUMENTS

| | | | | |
|---|---|---|---|---|
| 5,140,518 A | * | 8/1992 | Ema | 600/407 X |
| 5,452,416 A | * | 9/1995 | Hilton et al. | 345/424 X |
| 5,517,645 A | | 5/1996 | Stutz et al. | 709/316 |
| 5,776,050 A | * | 7/1998 | Chen et al. | 600/407 X |
| 6,101,407 A | * | 8/2000 | Groezinger | 600/407 |
| 6,177,937 B1 | * | 1/2001 | Stockham et al. | 600/407 X |
| 6,415,171 B1 | * | 7/2002 | Gueziec et al. | 600/407 |

OTHER PUBLICATIONS

Williams, et al. "The Component Object Model: A Technical Overview", Created Oct. 1994, http://www.microsoft.com/COM/wpaper/default.asp ("com: Technical Overview" link) 16 pg—printed Feb. 21, 2003.

* cited by examiner

Primary Examiner—Raymond J. Bayerl
(74) Attorney, Agent, or Firm—Fay, Sharpe, Fagan, Minnich & McKee, LLP

(57) ABSTRACT

A medical imaging display system includes a memory (40) for storing first image data representative of a region of interest. The memory (40) stores image data generated by medical imaging devices such as magnetic resonance devices (20), computed tomography devices (22), nuclear imaging devices (26,28,30), and ultrasound devices. Typically, image data from these devices is obtained some time prior to a surgical event and users may access this data in planning for the surgical event. A processor (42), in data communication with the memory, is organized under a component object modeling architecture. The processor (42) is connected to a user interface (10) for providing user requests to the processor. Thus, in response to user action via the user interface (10), the processor (42) determines an object (54) adapted to act on the request, selects a handle (60) for the determined object and, employs the object via the handle to act on the request. Additionally, the image guided surgical system also includes a source (48) of substantially real time image data generated in the surgical theater, such as spectroscopy devices, which can also be manipulated via software objects to display desired portions of the region of interest. Any of these images can be viewed on a display (46) in a planning environment, in the surgical suite, or even by a consultant, geographically remote from the surgical site.

23 Claims, 5 Drawing Sheets

METHOD AND APPARATUS FOR MEDICAL IMAGE DISPLAY FOR SURGICAL TOOL PLANNING AND NAVIGATION IN CLINICAL ENVIRONMENTS

BACKGROUND OF THE INVENTION

The present invention relates to the medical image display art. It finds particular application in connection with medical image displays in the surgical suite, and in the surgical planning stages where a need exists to quickly display large image files to enable an understanding of the anatomy of a patient, and thus will be described with particular reference thereto. It is to be appreciated however, that the invention will also find application in conjunction with other types of imaging where data on remote sensors is made available to a client via a component object model architecture.

Increasing amounts of information are available to medical personnel in the course of planning procedures and even during actual surgical events. Continued advances in medical imaging systems such as magnetic resonance imagers, computer tomography devices, nuclear imaging equipment, positron emission tomography and ultrasound often provide a variety of 2-D and 3-D image files of increasing size and optimized for imaging of specific environments. Often surgical planning requires reference to images obtained from one or more of the above listed imagers, and still other images are needed during the surgical procedure. Accordingly, image displays must be able to quickly access and manipulate image files. However, current display techniques have limitations due to large volumes of data associated with large imaged volumes, high resolution images, multiple images of a common volume from different imaging modalities, multiple temporally offset images of a common volume (ciné), the number of colors used, and other factors which make it difficult to optimize methods of accessing data from the memories of each of the above listed imagers. Moreover, utilizing the volumetric data of different imaging modalities is complex due to the different resolutions, different coordinates, different orthogonal and oblique planes, and the like.

surgical planning also requires deeper cut sections of the 3-D organs in multiple views to understand the anatomy of these organs. Typically, a series of planes across each proposed surgical path are indexed sequentially to understand the significance of a proposed path. The selected cut sections, slices, 3D renderings, and other views are typically needed rapidly in the clinical environment, particularly when a surgical procedure is in progress. This heavy burden on computer memory reduces display speed. The control of the data access diminishes as time progresses. Worse yet, the heavy data access and movement burden sometimes causes the computers to freeze removing the diagnostic tools from the physician conducting the planning process or the surgical procedure.

The present invention contemplates a new, improved method and apparatus for diagnostic image processing graphical and display which overcomes the above-referenced difficulties and others.

SUMMARY OF THE INVENTION

In accordance with an embodiment of the present invention, a method of medical imaging includes collecting medical image data, representative of a region of interest. Responsive to receipt of a request for manipulation of the image data, a software process is determined to at least partially accomplish the request. A handle for the determined process is selected, and the request is processed via the handle.

In accordance with another embodiment of the present invention, the method further includes displaying the processed image data.

In accordance with another embodiment of the present invention, the collecting image data step includes prior to a surgical event, receiving first image data from at least one medical imaging device. The medical imaging device is selected from the set of a magnetic resonance device, a computed tomography device, a nuclear imaging device, a Positron emission tomography device, and an ultrasound device. The first image data is then stored in a memory.

In accordance with another aspect of the present invention, the collecting image data step further includes during the surgical event receiving second image data, and storing the second image data in a memory.

In accordance with another aspect of the present invention, the request for manipulation of the image data includes an input from a user interface. The determining process step includes referencing a registry to detect the registration of a process adapted to accomplish the request. From the registry, a handle is noted associated with the process.

In accordance with another aspect of the present invention, the process resides in a component object modeling architecture and is adapted to make requests of other processes. The processing request step includes processing the request, and at determined locations in the process, formatting another request for another process to further accomplish the original request.

In accordance with another aspect of the present invention, the method further includes planning the surgical event by performing tasks, including manipulating the user interface to selectively control image data displayed.

In accordance with another aspect of the present invention, the method further includes performing the surgical event by performing tasks including manipulating the user interface to selectively control displays of the first and second image data.

In accordance with another embodiment of the present invention, a medical imaging system includes an imaging device for producing image data representative of a region of interest. A memory stores the image data and the processor manipulates at least portions of the image data for viewing on a display. A method of controlling the process includes the computer implemented steps of determining a process adapted to act on the request in response to a manipulation request from a client. A handle is determined which is associated with a component comprising the determined process, and the request is forwarded to the determined process via the handle.

In accordance with another aspect of the present invention, the determining a process step includes returning an identifier from a registry of identifiers. The returned identifier is associated with the component including the process.

In accordance with another embodiment of the present invention, a medical imaging display system includes a memory storing first image data representative of a region of interest. A processor in data communication with a memory is additionally connected to a user interface for manipulating portions of image data in response to requests. The processor is controlled by component object modeled software to (a)

determine an object adapted to act on the request, (b) select a handle for the determined object and, (c) employ the object via the handle to act on the request.

In accordance with another aspect of the present invention, the imaging display system further includes a display operatively connected to the processor which selectively displays the manipulated image data.

In accordance with another aspect of the present invention, the display system includes an image guided surgery planning system in which an operator selects views from the image data to plan a surgical event.

In accordance with another aspect of the present invention, the system further includes a source of substantially real time image data representative of the region of interest. A second object, selectively accessible to the processor, is adapted to manipulate the real time image data.

In accordance with another aspect of the present invention, the display system includes an image guided surgery system in which an operator selects views from the image data and real time image data to display during a surgical event.

One advantage of the present invention resides in the utilization of component object modeling architecture to improve the speed of display updates and appearance of the display during manipulation.

Another advantage of the present invention resides in the ability to perform remote surgery from a remote server.

Another advantage of the present resides in the system's flexibility to include other software, or third party software products within a COM-based architecture system.

Other advantages and benefits of the invention will become apparent to those skilled in the art upon a reading and understanding of the preferred embodiments.

BRIEF DESCRIPTION OF THE DRAWINGS

The invention may take physical form in certain parts and arrangements of parts, and in various steps and arrangements of steps. The drawings are only for purposes of illustrating a preferred embodiments and is not to be construed as limiting the invention.

DETAILED DESCRIPTION OF THE PREFERRED EMBODIMENTS

Figure 1:
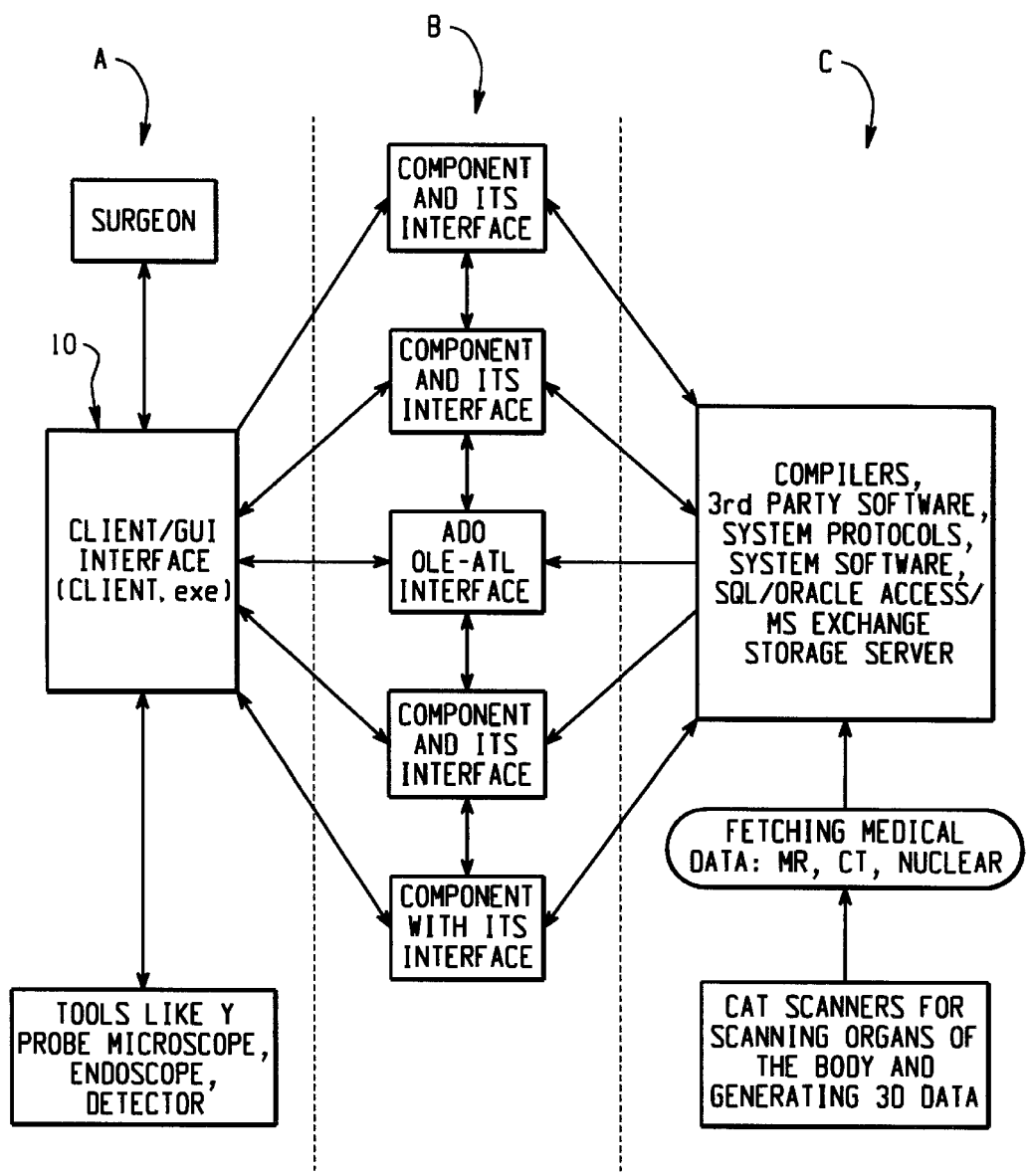
FIG. 1 is an overview block diagram of a medical imaging system for surgical tool planning/navigation based on component object modeling architecture.

FIG. 1 shows an exemplary 2D medical image processing and 3D, 4D high speed medical image display using control based COM-architecture for an NT operating system. The COM based layout can be understood as consisting of three layers: the Graphical User Interface layer A, the COM-architecture layer B, and the server layer C. The GUI interface layer A includes a graphical user interface 10 which an operator uses to interact with image data using a computer mouse, for example. The COM-architecture layer B is the main software layer where the core applications are written in an object oriented language such as C++. This layer is also referred to as the software layout layer, since it is the foundation of the system. Those skilled in the art recognize that constructing the COM-architecture layer B according to the COM based architecture enables COM based concepts to be employed, for example in manipulating image data. These concepts are threading, category manager, component category, containment, aggregation, encapsulation, inheritance, polymorphism, over-riding, class factory, apartment and free threading, marshaling of data, and the like. Moreover, artisans will appreciate that a COM-architecture layer so constructed will have improved display performance and increased stability as will be more fully discussed below. The server layer C, contains system and image data information. Typically, medical image data is stored in this layer in DICOM format. This layer also desirably enables various connections to other platforms.

Figure 2:
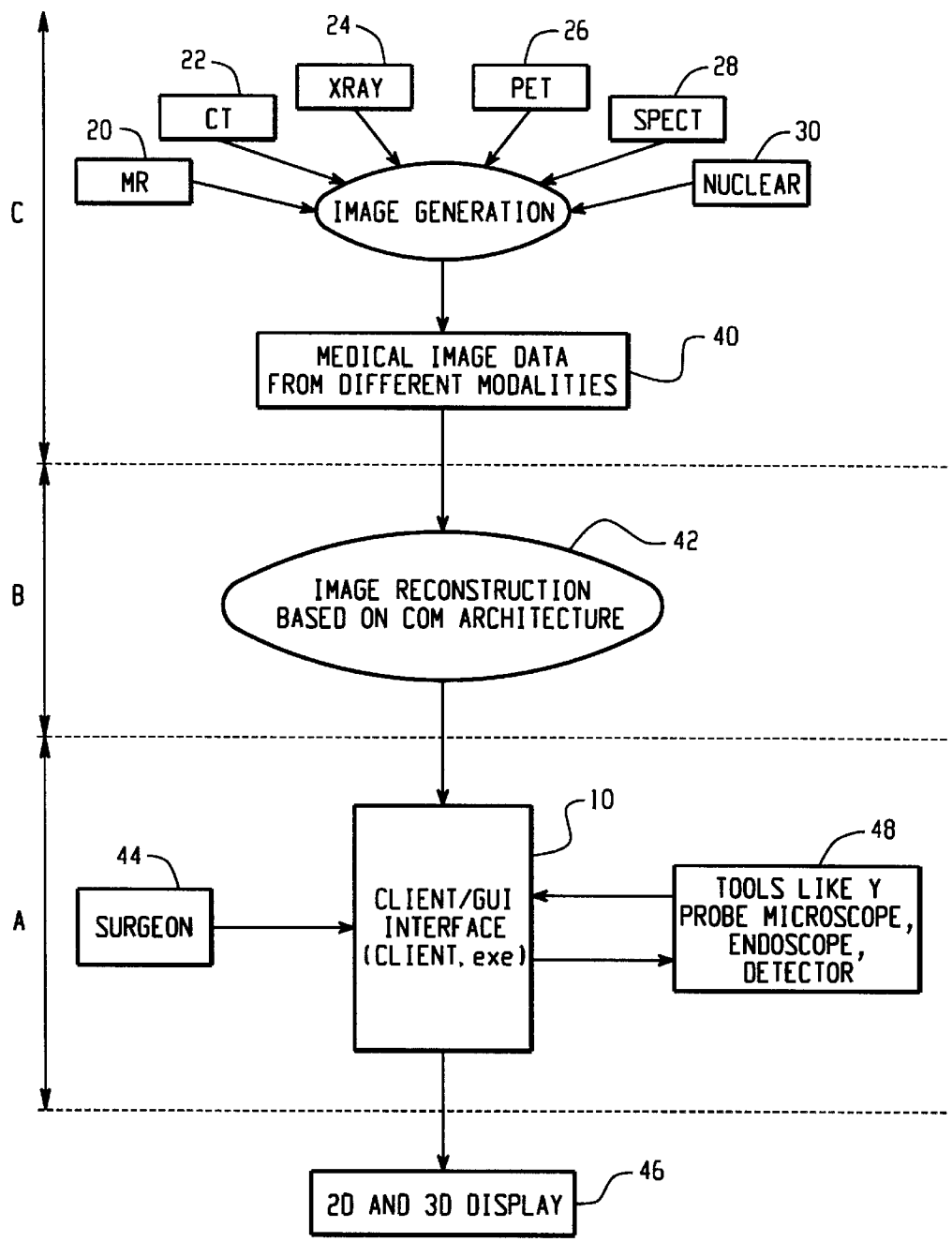
FIG. 2 is a more detailed diagram of the system of FIG. 1.

Reference to FIG. 2, illustrates several such other platforms connectable to server layer C. These platforms include a magnetic resonance imaging (MRI) system 20, a computerized tomography (CT) scanner 22, a digital x-ray radiographic or fluorographic system 24, a positron emission tomography (PET) scanner 26, a single photon emission computed tomography (SPECT) scanner 28, and a nuclear imaging system 30. However, those skilled in the art will appreciate other known and yet to be developed imaging modalities can be employed analogously. That is, any image data generation equipment can be used without loss of functionality in the present invention. Typically, images are collected one at a time from one, two, or all of the above-mentioned image generation systems. The image data from these systems are segregated and stored into a memory for reconstruction and manipulation. Those skilled in the art will appreciated that while the illustration shows medical image data collected into a common memory 40, the image data alternatively can reside within plural central, or regional memories or memories physically associated with each individual imaging device and mutually accessible, for example, over a network.

The COM-architecture layer B includes a plurality of components and interfaces constructed in a component object modeling (COM) architecture but written in any compatible software programming language. For ease of illustration, the plurality of components and interfaces of the COM-architecture layer B are grouped in a generic reconstruction block 42. The graphical user interface layer A is provided to manipulate individual processes within the image reconstruction block 42. For example, a physician 44 selects a particular slice from a previously acquired and stored computerized tomography image via the interface 10. The user interface 10 selects the appropriate process from the plurality of components in the image reconstruction processor 42 for display 46. Additionally, surgical tools or in-suite imaging systems 48 (for example, spectroscopy systems) also interfaced through component object modeling architecture have their resultant images registered and overlaid with user selected images, enabling the physician to compare real time images with previously acquired images to obtain surgical probe location feedback during an image guided surgery (IGS) procedure.

Figure 3:
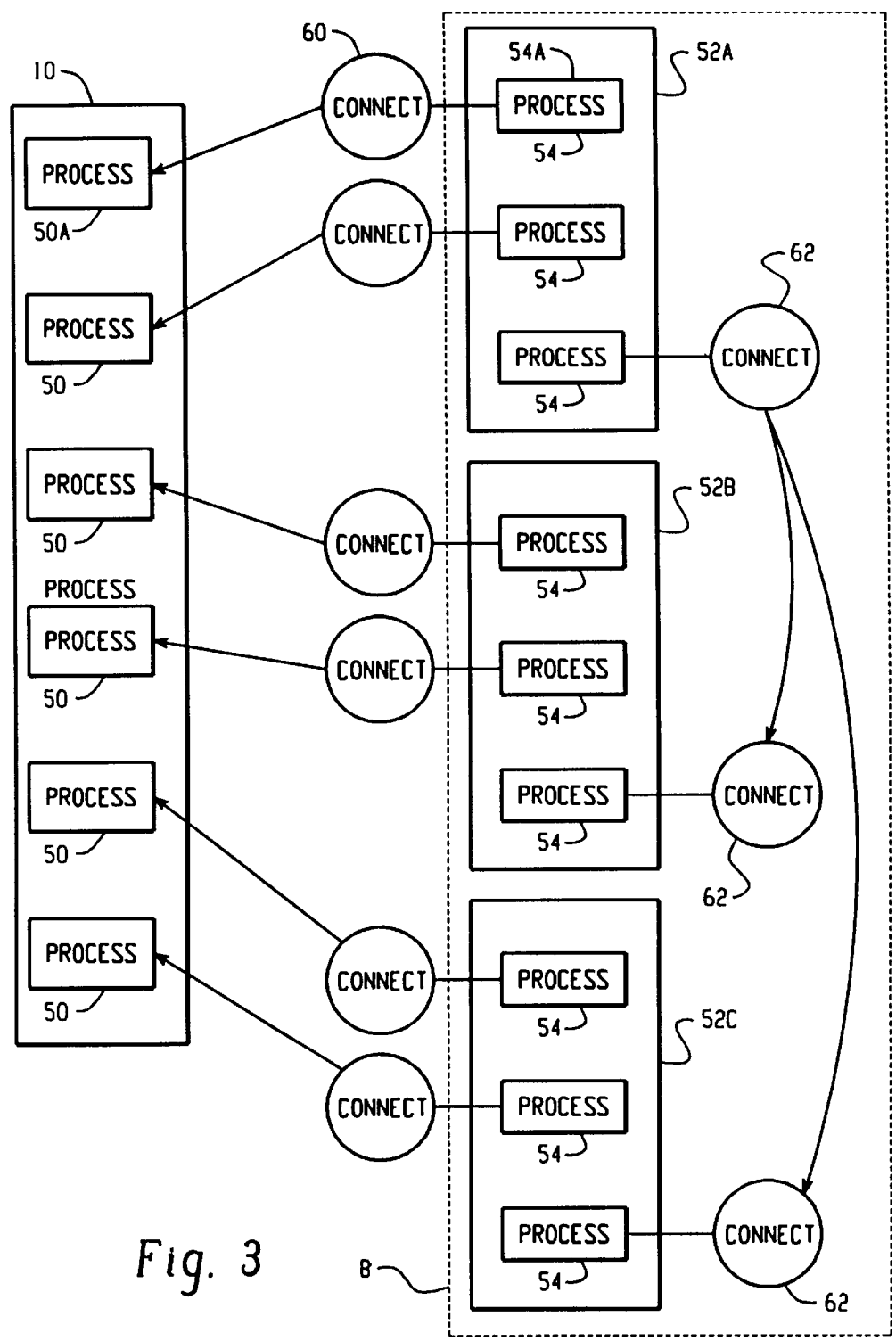
FIG. 3 is an exemplary illustration of a medical imaging display layout providing communication between components in accordance with the present invention.

Referring now to FIG. 3, the interface 10 includes a plurality of processes or algorithms 50 each performing a variety of preprogrammed procedures, such as generating a screen with a 3D rendering and transverse sagittal and coronal slices through a selected point in the rendered object. When an individual process 50A, for example, reaches a point on a local instruction set or task requiring interaction with another component, a determination of the availability of the other component is made. To continue the previous example, process 50A can be thought of as requesting a 3D rendering to rotate. This rotation process, if available, can reside for example in the COM-architecture layer B which also includes a plurality of individual components 52A, 52B, 52C. These components 52A, 52B, 52C are further comprised of a number of processes 54, for example, rotation, coronal slice generation, placement of multiple slices on a single screen, and the like. Moreover the processes 50 contained in the interface 10 can represent, for example, individual display commands such as selecting different image views, manipulating certain image views, and/or arranging various image views on a display screen. Thus, in response to the process 50A reaching a point in the algorithm requiring action by a separate object, the rotational process 54 within the component 52A is determined. The initiating process 50A then selects a handle or identifier 60 for the rotation process 54A which is capable of performing the task.

Those skilled in the art will appreciate that individual handles 60 are cataloged in a registry table as objects within certain processes are created or instantiated. Details of the registry table interacting with individual objects are known to those skilled in the art. Moreover, artisans appreciate that within components 52A, 52B, 52C, individual processes 54 also allocate tasks among various other processes, a property known as Containment. Indeed providing a COM-architecture for the various components 52A, 52B, 52C in the architecture layer B provides other handles 62 allowing task sharing between processes within different components 52A, 52B, 52C. This property is known as Aggregation. In other words, the property known as Aggregation enables use of one piece of code in multiple COM processes having a common handle 60.

Figure 4:
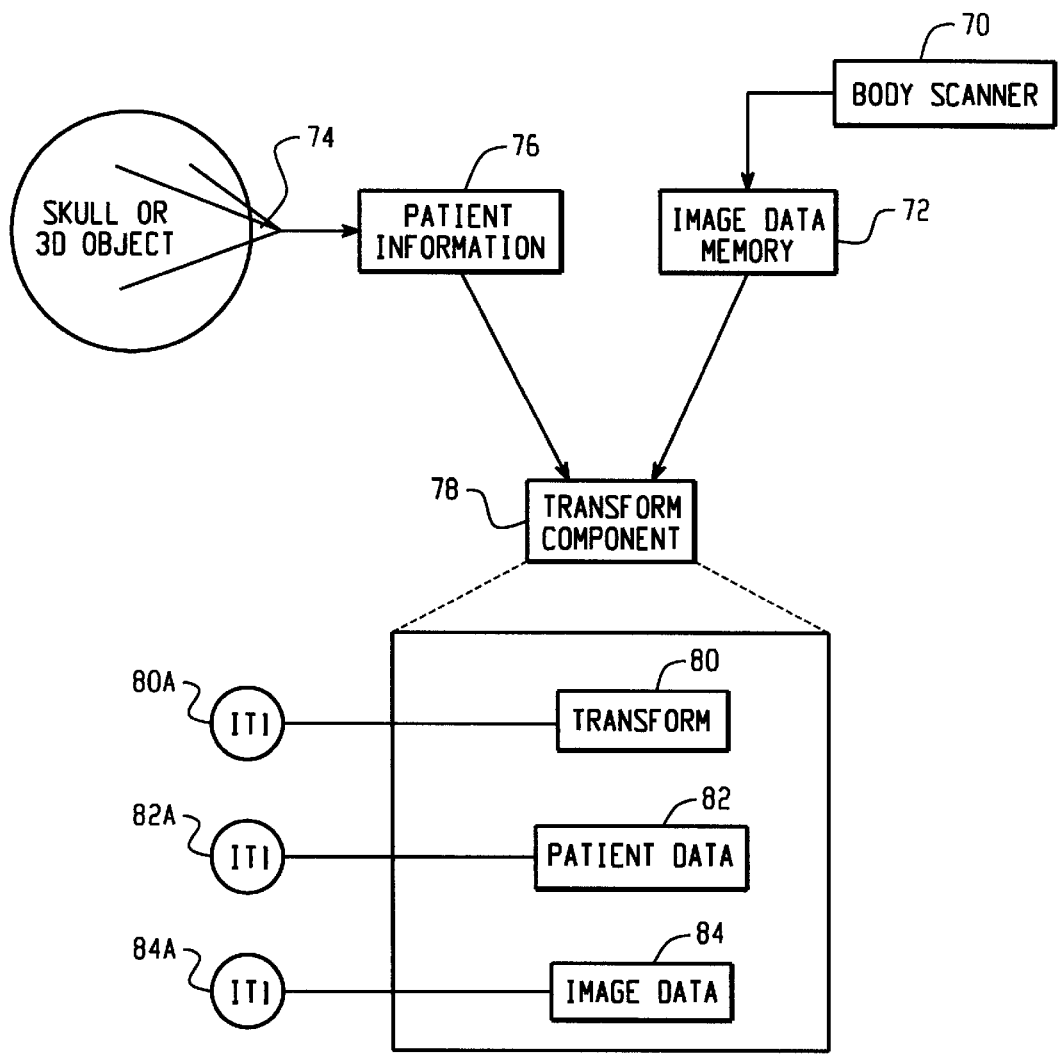
FIG. 4 illustrates an exemplary system to register images between real time patient data and previously obtained image data; and, FIG. 5 illustrates an exemplary relationship between a graphical user interface and corresponding image displays.

Referring now to FIG. 4, the property of COM Containment is illustrated in a registration process between a previously obtained image and a real time image. Sometime prior to commencement of a medical procedure, an area of interest is imaged in a medical imaging device such as a CT or other body scanner 70. This image data is reconstructed conventionally and stored into an image data memory 72 for later evaluation and/or use. Later, for example within the surgical suite during the procedure, additional patient imaging information is collected by other imaging apparatus such as a Y-probe 74. This image data is also conventionally processed and stored in a patient information file 76. A transform component 78 resides within, or is accessible to, the user interface 10. (FIGS. 1, 2). Again, the benefits of a COM-architecture enable various processes to perform specific tasks. In the illustrated example, a transform process 80 is invoked to register or align the current and reference images from the image data memory 72 and the patient information file 76 prior to display. The transform process is accessed through its handle 80A. Within the exemplary transform process a selected view is required from the patient information 76. The transform process 80 formats a request performable by a patient data process 82. The patient data process 82 is accessed through its handle 82A. Additionally, the transform process 80 in this example, also must manipulate certain previously acquired image data 72. Thus, the image data process 84 receives the task generated by the transform process 80 through its image data handle 84A. Continuing with the example, when the transform process 80 either receives the desired information back, or other notice of sub-task completion, for example by receipt of pointers toward a storage location, the transform process 80 proceeds with its task as programmed.

Figure 5:
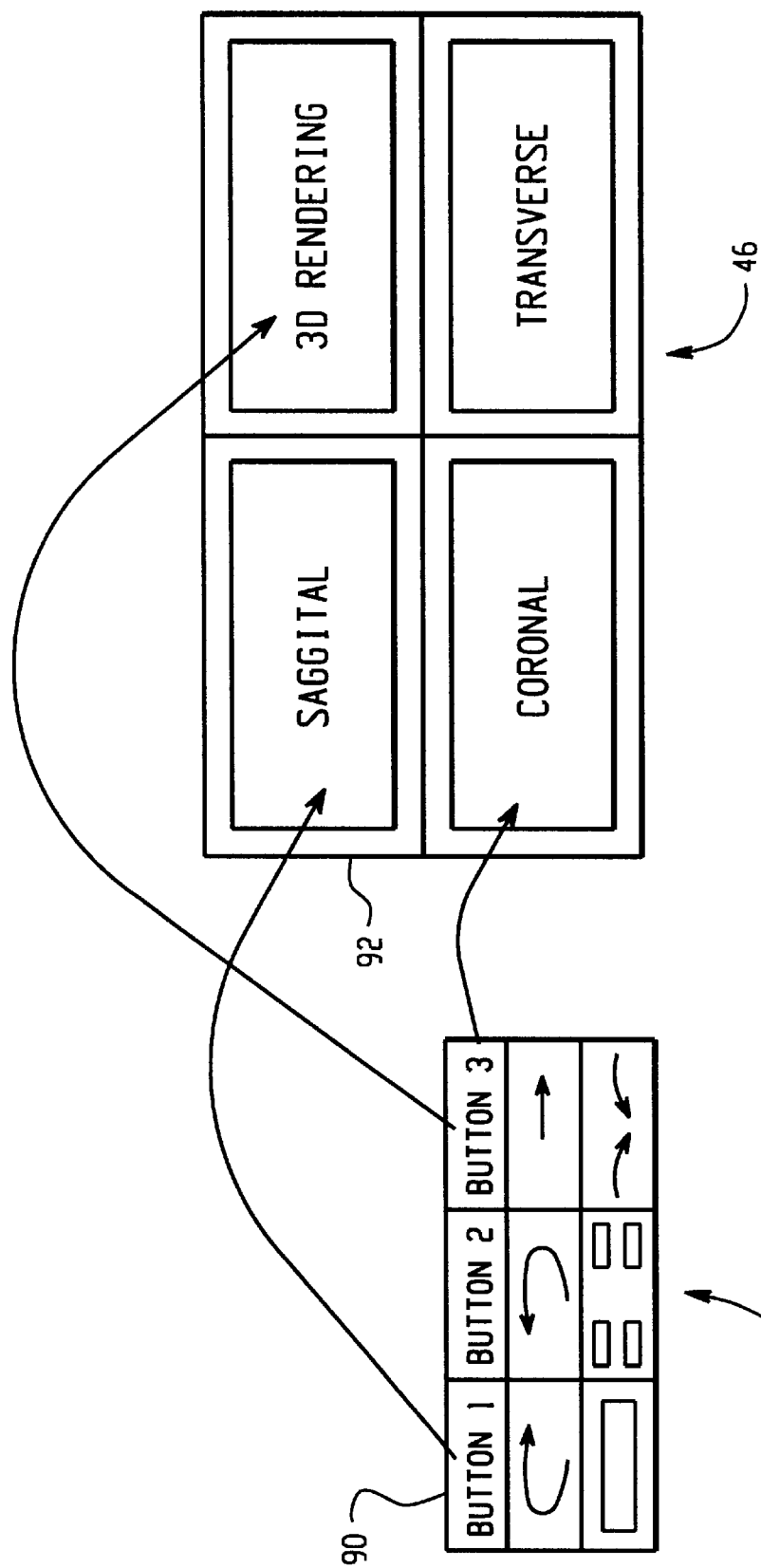

Referring now to FIG. 5, an exemplary version of the graphical user interface 10 controls the image displayed on the display 46. As illustrated, buttons, icons or other interface tools are positioned for manipulation by a user to control images on display 46. For example, a button 90 is programmed to toggle or select certain images at a location 92 in the image display 46. Those skilled in the art will appreciate that a similar association can be achieved through other buttons in the interface. Additional flexibility can be programmed into the interface allowing an operator to rotate a selected image, superimpose several image sources, and perform other display combinations or manipulations.

The invention has been described with reference to the preferred embodiments. Modifications and alterations will occur to others upon a reading and understanding of the preceding detailed description. It is intended that the invention be construed as including all such modifications and alterations insofar as they come within the scope of the appended claims or the equivalents thereof.

Having thus described the preferred embodiment, the invention is now claimed to be:

1. A method of displaying medical images, the method including:

responsive to receipt of a request for manipulation of image data representative of a region of interest, determining a component object within a component object model architecture, which component object is configured to at least partially accomplish the request;

selecting a handle for an interface to the determined component object; and processing the request via the handle.

2. The method as set forth in claim 1, further including displaying the processed image data.

3. The method as set forth in claim 1, further including:

receiving first image data from at least one medical imaging device selected from the set of a magnetic resonance device, a computed tomography device, a nuclear imaging device and an ultrasound device; and storing the first image data in a memory.

4. The method as set forth in claim 3, wherein the method further includes planning a surgical event by performing tasks including manipulating a user interface to selectively control image data displayed.

5. The method as set forth in claim 3, further including:

receiving second image data; and storing the second image data in a memory.

6. The method as set forth in claim 5, wherein the method further includes performing a surgical event by performing tasks including manipulating a user interface to selectively control display of first image data and second image data.

7. The method as set forth in claim 1, wherein the determining a process step includes:

referencing a registry to detect registration of a process adapted to accomplish the request; and noting the handle associated with the process.

8. The method as set forth in claim 1, wherein the component object is determined from a plurality of component objects within the component object model architecture, the processing of the request including:

selecting a second handle for an interface to a second component object; and formatting a second request directed to the second component object using the second handle to perform at least a portion of the processing.

9. A diagnostic imaging system comprising:
- an image memory system for storing a plurality of volume digital image representations reconstructed from diagnostic data generated by a plurality diagnostic imagers;
- a user interface through which a user selects among image display formats;
- a component object modeling (COM) architecture layer which includes image processing components for retrieving portions of the digital image representations and processing the retrieved portions into the selected display format.

10. The diagnostic imaging system as set forth in claim 9 wherein:
- the user interface includes a component ID registry table which correlates user selected display formats with IDs of selected components for retrieving and processing the portions of the image representations.

11. The diagnostic imaging system as set forth in claim 10 wherein:
- at least some of the components identify other components which they access and cooperate with to process the portion of the image representations.

12. An image guided surgical system for use by a surgeon in performing an image-assisted surgical procedure on a surgical area of a subject, the surgical system including:
- a real time surgical imaging system operated by the surgeon to acquire real-time images of the surgical area;
- a database of diagnostic images of the surgical area acquired prior to the surgical procedure, the diagnostic images including images in a format different from that of the real-time images;
- a component object model architecture software layer for performing image processing, the component object model architecture software layer containing a plurality of component objects, each component object being configured to perform a selected image processing task and having at least one interface accessible by a handle; and
- a graphical user interface that receives the real-time images and performs image display processing including at least registering a real-time image with at least one diagnostic image, the graphical user interface delegating at least some of the image display processing to one or more selected component objects of the component object model architecture software layer by interfacing with the selected component objects via handles of the selected component objects.

13. The surgical system as set forth in claim 12, wherein the database of diagnostic images includes diagnostic images acquired using at least two different imaging modalities.

14. The surgical system as set forth in claim 12, wherein the database of diagnostic images includes diagnostic images acquired using at least two different imaging modalities selected from a group consisting of: magnetic resonance (MR) imaging, computed tomography (CT) imaging, x-ray imaging, fluoroscopic imaging, positron emission tomography (PET) imaging, single photon emission computed tomography (SPECT) imaging, nuclear imaging, and ultrasound imaging.

15. The surgical system as set forth in claim 12, wherein the surgical probe includes an endoscope.

16. The surgical system as set forth in claim 12, wherein the component objects of the component object model architecture software layer include a component object selected from a group consisting of: a 3D rendering rotation component object, an image registration component object, an image overlay component object, an image view selection component object, and an image view display arrangement component object.

17. The surgical system as set forth in claim 12, wherein the component objects of the component object model architecture software layer include:
- an aggregation component object defined by aggregation of at least two other component objects.

18. The surgical system as set forth in claim 12, wherein the component objects of the component object model architecture software layer include:
- a containment component object that contains at least one other component object.

19. A image-guided surgical method including:
- acquiring a real-time surgical image during a surgical procedure;
- selecting a display format that includes displaying the real-time surgical image and at least one stored diagnostic image;
- interfacing with a component object modeling architecture software layer using handles to selected component objects of said software layer to compute display data; and
- generating a display based on the display data.

20. The surgical method set forth in claim 19, wherein the interfacing includes:
- aggregating a plurality of component objects to define an aggregate component object; and
- interfacing with the aggregate component object using a handle of the aggregate component object.

21. The surgical method set forth in claim 19, further including:
- allocating at least some of the computing of the display data to a component object contained by one of the selected component objects.

22. An image guided surgical system for use in performing an image-assisted surgical procedure, the surgical system including:
- a real time imager that provides real-time images in a first format of a surgical area;
- a database of diagnostic images of the surgical area acquired prior to the surgical procedure using one of at least two selectable imaging modalities, the diagnostic images including images in a second format different from the first format of the real-time images;
- a component object model architecture software layer for performing image processing, the component object model architecture software layer including a plurality of component objects, each component object being configured to perform a selected image processing task and having at least one interface accessible by a handle, the component object model architecture supporting at least component aggregation and component containment; and
- a graphical user interface that receives the real-time images and performs image display processing including at least combining a real-time image with at least one diagnostic image, the graphical user interface delegating at least some of the image display processing to one or more selected component objects of the com ponent object model architecture software layer by interfacing with the selected component objects via handles of the selected component objects.

23. The image guided surgical system as set forth in claim 22, wherein the one or more selected component objects include:

an image processing component configured to process diagnostic images from any of the at least two selectable imaging modalities, the image processing component object including a first imaging modality component object configured to process images from a first of the at least two selectable imaging modalities and a second imaging modality component object configured to process images from a second of the at least two selectable imaging modalities, the first and second imaging modality component objects combining to contribute to the image processing component object by one of aggregation and containment.

* * * * *